(12) United States Patent
Mikalo et al.

(10) Patent No.: US 9,613,181 B2
(45) Date of Patent: Apr. 4, 2017

(54) SEMICONDUCTOR DEVICE STRUCTURE INCLUDING ACTIVE REGION HAVING AN EXTENSION PORTION

(71) Applicant: GLOBALFOUNDRIES Inc., Grand Cayman (KY)

(72) Inventors: Ricardo Pablo. Mikalo, Heideblick (DE); Joachim Deppe, Dresden-Langebrueck (DE)

(73) Assignee: GLOBALFOUNDRIES Inc., Grand Cayman (KY)

( * ) Notice: Subject to any disclaimer, the term of this patent is extended or adjusted under 35 U.S.C. 154(b) by 0 days.

(21) Appl. No.: 14/719,424

(22) Filed: May 22, 2015

(65) Prior Publication Data

US 2015/0349120 A1    Dec. 3, 2015

(51) Int. Cl.
| | |
|---|---|
| *H01L 27/088* | (2006.01) |
| *G06F 19/00* | (2011.01) |
| *H01L 29/78* | (2006.01) |
| *H01L 27/12* | (2006.01) |
| *H01L 29/417* | (2006.01) |

(52) U.S. Cl.
CPC ........ *G06F 19/321* (2013.01); *G06F 19/3443* (2013.01); *H01L 27/088* (2013.01); *H01L 27/1207* (2013.01); *H01L 29/41766* (2013.01); *H01L 29/7835* (2013.01)

(58) Field of Classification Search
CPC .......... H01L 29/66545; H01L 29/7835; H01L 27/1207; H01L 29/41766; H01L 27/088; H01L 27/0207
See application file for complete search history.

(56) References Cited

U.S. PATENT DOCUMENTS

2007/0057340 A1*  3/2007  Jung ................... H01L 29/0692
257/510

* cited by examiner

*Primary Examiner* — Khiem D Nguyen
(74) *Attorney, Agent, or Firm* — Amerson Law Firm, PLLC (57) ABSTRACT

A semiconductor device structure includes a semiconductor substrate with an active region provided therein, a gate structure, a dummy gate structure and two contact regions provided in the active region for forming source and drain regions. The gate structure and the dummy gate structure are formed on the semiconductor substrate so as to partially overlie the active region, and one of the contact regions is located at one side of the dummy gate structure. The semiconductor device structure includes a contact structure contacting one of the contact regions and the dummy gate for connecting this contact region and the dummy gate to one of a Vdd rail and a Vss rail. The active region has an extension portion protruding laterally away from the active region relative to the other contact region, where the contact structure is located over the extension portion.

17 Claims, 5 Drawing Sheets

SEMICONDUCTOR DEVICE STRUCTURE INCLUDING ACTIVE REGION HAVING AN EXTENSION PORTION

BACKGROUND OF THE INVENTION

1. Field of the Invention

The present disclosure relates to semiconductor device structures and, more particularly, to a layout of gate structures and contact structures of semiconductor device structures.

2. Description of the Related Art

In modern electronic equipment, integrated circuits (ICs) experience a vast applicability in a continuously spreading range of applications. In particular, the demand for increasing mobility of electronic devices at high performance and low energy consumption drives developments to more and more compact devices having features with sizes significantly smaller than 1 μm, the more so as current semiconductor technologies are apt of producing structures with dimensions in the magnitude of 100 nm or less. With ICs representing a set of electronic circuit elements integrated on a semiconductor material, normally silicon, ICs may be made much smaller than any discreet circuit composed of separate independent circuit components. Indeed, the majority of present-day ICs are implemented by using a plurality of circuit elements, such as field effect transistors (FETs), also called metal oxide semiconductor field effect transistors or MOSFETs, occasionally also simply referred to as MOS transistors, and passive elements, such as resistors, e.g., diffusion resistors, and capacitors, integrated on a semiconductor substrate within a given surface area. Typical present-day ICs involve millions of single circuit elements formed on a semiconductor substrate.

In the design and fabrication of advanced ICs, an IC is represented by means of so-called IC layouts indicating planar geometric shapes which correspond to the pattern of metal, oxide or semiconductor layers that make up the components of the integrated circuit. Standard processes for fabricating advanced ICs are based on well-known and well-understood interactions of many chemical, thermal and photographic variables which are carefully controlled and on which the behavior of the final IC largely depends. Important variables herein are given by positions and interconnections of the geometric shapes of the various layers used to build components of ICs.

Usually, when designing an IC, the components intended for making up a microchip are placed and connected in an IC layout such that the final chip meets certain criteria, typically: performance, size, density and manufacturability. On the basis of the data as provided by an IC layout, semiconductor foundries generate photomasks to be used in the various photolithography processes employed in current process flows.

It is typically checked whether the layout satisfies a series of recommended parameters (called design rules) before sending the layout of ICs to semiconductor foundries. The design rules are provided by semiconductor manufacturers as a series of parameters and enable the designer to verify the correctness of a mask set. For example, a set of design rules specifies certain geometric and connectivity restrictions to provide sufficient margins accounting for variability in semiconductor manufacturing processes. In this way, it is ensured that most of the parts work correctly.

Driven by Moore's Law, there is an ongoing challenge in the semiconductor industry to reduce the area consumed by layouts based on cost and performance aspects. As a consequence, technology nodes of present ICs are constantly shrinking as much as possible. With shrinking technology nodes, the physical effects become more and more important, such as, for example, mechanical stress, contact etch behavior and the like. Additionally, the downscaling of semiconductor devices causes electrical fields with certain geometric dimensions. With the dimensions of advanced semiconductor devices being smaller than 65 nm, the electrical behavior of transistor devices cannot only be treated as being solely dependent on the width and length dimension of a transistor. For example, upon reaching the 28 nm technology node, the electrical behavior of transistors was observed to depend on design rules defining a great number of geometric dimensions and shapes of the various features in complex semiconductor devices, as will be described below with regard to FIG. 1.

Figure 1:
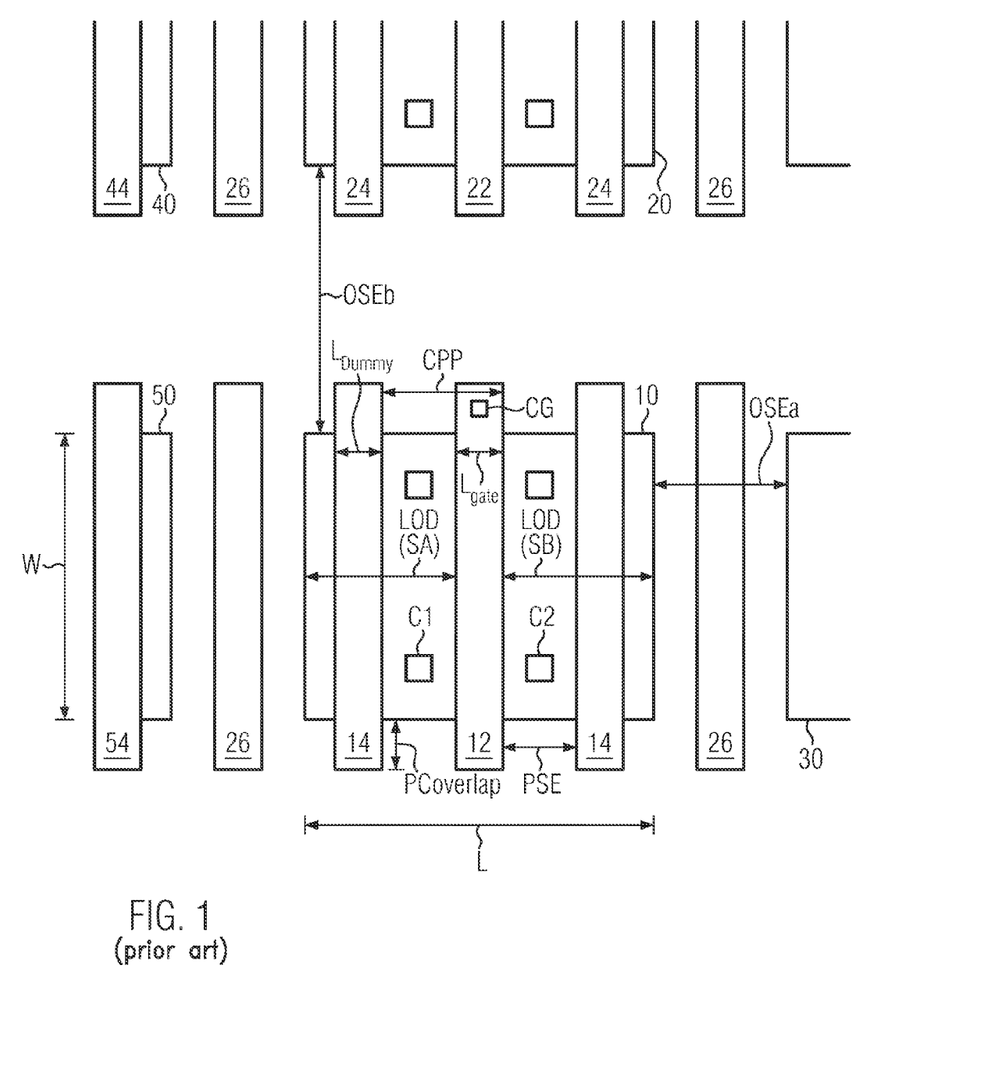
FIG. 1 schematically illustrates a conventional IC layout.

FIG. 1 shows in a top view a semiconductor device structure having a plurality of active regions 10, 20, 30, 40 and 50. In each of the active regions 10, 20, 30, 40 and 50, gates overlying the active regions are formed, e.g., gate 12 and dummy gates 14 over the active region 10, gate 22 and dummy gates 24 over the active region 20, dummy gate 44 over the active region 40, and dummy gate 54 over the active region 50. Typically, dummy gates are formed to reduce production tolerances.

By means of the following design rules (depending on the technology node), a semiconductor foundry allows designers to design only the layout pattern as seen in the top view, while thicknesses of layers are fixed by the semiconductor foundry. The design rules will be explained relative to the active region 10. For example, the geometry and shape of the active region and the gates are set on the basis of the following parameters, as illustrated in FIG. 1: W, L, OSEa defining a separation between adjacent active regions parallel to the length dimension L, OSEb setting a spacing between adjacent active regions parallel to the W dimension, PSE setting a spacing between two neighboring gate structures 12, 14, within an active region, CPP ("contacted poly pitch") setting a repetitive spacing between two neighboring gates including a length of the gates and dummy gates parallel to the L dimension, LOD (SA) defining a minimum spacing between an active gate structure 12 and a boundary of the active region 10 to the left side (parallel to the L dimension), LOD (SB) defining an according spacing between an active gate 12 and a boundary of the active region 10 to the right side (parallel to the L dimension), and the PC overlap setting margins and overlap of the gate structures 12, 14 relative to the active region 10. Length dimensions of the gate structures 12 and the dummy gate structures 14 are indicated in FIG. 1 via $L_{gate}$ and $L_{dummy}$, respectively. The aforementioned design rules are not limiting and further design rules may be imposed by the semiconductor foundry to define the geometry and shape of source/drain contacts C1, C2 and gate contacts CG.

From the above description, it is therefore desirable to provide a semiconductor device structure allowing small layout standard cell footprints in VLSI ("very large scale integration") layouts at 28 nm and below, without giving raise to area penalty.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

The present disclosure proposes, in some illustrative aspects, a way of realizing small layout standard cell footprints in VLSI layouts at 28 nm and below, without giving raise to area penalty. In some illustrative embodiments of the present disclosure, layout limitations are introduced and ways of realizing active shut down of dummy gate structures is provided without deteriorating the electronic properties of ICs at large VLSI scales via suitable connections for dummy gate structures and source/drain regions.

In a first aspect of the present disclosure, a semiconductor device structure is provided. In accordance with some illustrative embodiments herein, the semiconductor device structure includes a semiconductor substrate with an active region provided therein, a gate structure and a dummy gate structure. The semiconductor device further includes two contact regions that are provided in the active region for forming source and drain regions, each of which being located at a respective one of two opposing sides of the gate structure. The gate structure and the dummy gate structure are both formed on the semiconductor substrate, so as to partially overlie the active region, and one of the contact regions is further located at one side of the dummy gate structure. Additionally, the semiconductor device structure includes a contact structure contacting the one of the contact regions and the dummy gate structure for connecting this contact region and the dummy gate structure to one of a Vdd rail and a Vss rail. In a top view of the active region, the active region has an extension portion protruding laterally away from the active region relative to the other contact region, where the contact structure is located over the extension portion.

In a second aspect of the present disclosure, a semiconductor device structure is provided. In accordance with some illustrative embodiments herein, the semiconductor device structure includes a semiconductor substrate with an active region provided therein, and at least first and second gate structures and first and second dummy gate structures, the gate structures and dummy gate structures being formed on the semiconductor substrate so as to partially overlie the active region, wherein the gate structures and the dummy gate structures are provided in a successive manner. The semiconductor substrate further includes at least five contact regions that are provided in the active region such that each of the gate structures and each of the dummy gate structures have respective source and drain regions formed at opposing sides thereof, each of which being located at a respective one of two opposing sides of one of the gate structures, wherein one of the contact regions is further located at one side of a respective one of the first and second dummy gate structures, and at least two contact structures, each of which contacting one of the contact regions that is enclosed by one of the gate structures and one of the dummy gate structures for connecting the respective one of the contact regions together with a respective one of the dummy gates to one of a Vdd rail and a Vss rail. In a top view of the active region, the active region has at least two extension portions protruding laterally away from the active region relative to the other contact region, the contact structure being located over the extension portion, and wherein, between two successive contact portions with a respective one of the extension portions, there is one contact portion without extension portion.

BRIEF DESCRIPTION OF THE DRAWINGS

The disclosure may be understood by reference to the following description taken in conjunction with the accompanying drawings, in which like reference numerals identify like elements, and in which:

FIG. 2b schematically illustrates an interconnection pattern between a gate structure and adjacent dummy gate structures of the embodiment shown in FIG. 2a;

FIG. 2d schematically illustrates a cross-section view along a line a-a in FIG. 2a;

FIG. 2e schematically illustrates a cross-section view along the line b-b in FIG. 2a.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present disclosure will now be described with reference to the attached figures. Various structures, systems and devices are schematically depicted in the drawings for purposes of explanation only and so as to not obscure the present disclosure with details which are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary or customary meaning as understood by those skilled in the art, is intended to be implied by consistent usage of the term or phrase herein. To the extent that a term or phrase is intended to have a special meaning, i.e., a meaning other than that understood by skilled artisans, such a special definition shall be expressively set forth in the specification in a definitional manner that directly and unequivocally provides the special definition for the term or phrase.

The present disclosure relates to a method of forming a semiconductor device and to semiconductor devices, wherein the semiconductor devices are integrated on or in a chip. In accordance with some illustrative embodiments of the present disclosure, the semiconductor devices may substantially represent FETs, e.g., MOSFETs or MOS devices. When referring to MOS devices, the person skilled in the art will appreciate that, although the expression "MOS device" is used, no limitation to a metal-containing gate material and/or to an oxide-containing gate dielectric material is intended.

Semiconductor devices of the present disclosure concern devices which are fabricated by using advanced technologies, i.e., the semiconductor devices are fabricated by technologies applied to approach technology nodes smaller than 100 nm, for example, smaller than 50 nm or smaller than 35 nm, e.g., at 28 nm or below. The person skilled in the art will appreciate that, according to the present disclosure, ground rules smaller or equal to 45 nm, e.g., at 28 nm or below, may be imposed. The person skilled in the art will appreciate that the present disclosure proposes semiconductor devices with structures of minimal length dimensions and/or width dimensions smaller than 100 nm, for example, smaller than 50 nm or smaller than 35 nm or smaller than 28 nm. For example, the present disclosure may provide semiconductor devices fabricated by using 45 nm technologies or below, e.g., 28 nm or even below.

The person skilled in the art will appreciate that semiconductor devices may be fabricated as P-channel MOS transistors or PMOS transistors and N-channel transistors or NMOS transistors; both types of transistors may be fabricated with or without mobility-enhancing stressor features or strain-inducing features. It is noted that a circuit designer can mix and match device types, using PMOS and NMOS devices, stressed and unstressed, to take advantage of the best characteristics of each device type as they best suit the semiconductor device under design.

From the discussion of FIG. 1 above, it is apparent that, with increased scaling towards technology nodes at VLSI scales, such as for FDSOI (Fully Depleted Silicon On Insulator) techniques at 22 nm, 14 nm or even below, there is a great number of design rules. In accordance with some illustrative embodiments of the present disclosure, it is proposed to introduce certain layout limitations at 28 nm and below. For example, limitations on design rules may be obtained by employing a "continuous RX" design, where a "continuous active region" is formed, as will be described below with regard to FIG. 2a. The term "continuous RX" as used herein generally refers to an active region where several transistors are placed aside from each other without any interrupting isolation grooves, i.e., the active region is continuous. The person skilled in the art will appreciate that the application of continuous RX designs for active regions is not limited to FDSOI techniques, but may be also employed in bulk or hybrid techniques.

Figure 2A:
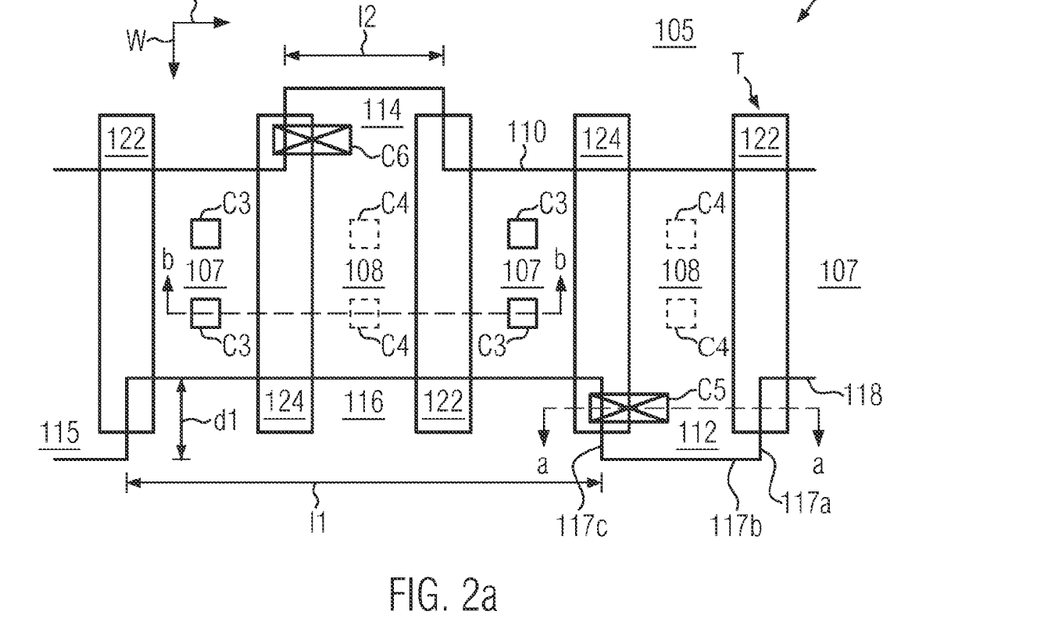
FIG. 2a schematically illustrates an IC layout in accordance with some illustrative embodiments of the present disclosure.

FIG. 2a schematically illustrates an illustrative IC layout in accordance with some illustrative embodiments of the present disclosure. The IC layout 100 has an active region 110 which is provided in a substrate 105. The active region 110 may be, in accordance with some illustrative examples herein, provided as a doped region of a semiconductor substrate 105 that is laterally enclosed by an isolation structure (not illustrated), e.g., an STI structure. The substrate 105 may be a bulk substrate or an SOI substrate, where a semiconductor film is provided over a buried insulating material layer, which in turn is formed over a base substrate, e.g., silicon and the like. For example, SOI substrates may be realized by means of FDSOI substrates having semiconductor films with a thickness of 20 nm or less, buried insulating material layers with a thickness of 145 nm or a thickness in a range from 10-30 nm over a base semiconductor substrate, such as a base silicon substrate. In case of FDSOI structures, the active region 110 is preferably not doped and laterally enclosed by an insulating structure (not illustrated).

In some illustrative embodiments of the present disclosure, the active region 110 may have a length dimension L that is substantially greater than a minimum width dimension W. For example, an aspect ratio L/W may be substantially bigger than 1, 2, 5, 10, etc. The person skilled in the art will appreciate that, in some illustrative examples herein, layout limitations may be introduced for IC layouts 100 at VLSI scales at 28 nm or below by choosing the aspect ratio of L/W being substantially greater than 5, 10, 20, etc. in order to implement the "continuous RX" design referred to above. Particularly, active regions, in accordance with the "continuous RX" design, may be strip-like and comprise a plurality of gate structures 122, 124, e.g., in the order of 10 gate structures or more, such as 15 or 20 or 30, etc.

As illustrated in FIG. 2a, gate structures 122 and dummy gate structures 124 are formed in a successive manner such that a gate structure 122 has two neighboring dummy gate structures 124 located at opposing sides of the gate structure 122. Furthermore, at opposing sides of each gate structure 122, contact regions 107, 108 are provided in order to implement source and drain regions for the gate structure 122. The person skilled in the art will appreciate that the contact regions 107 and 108 may be, for example, provided in FDSOI implementations by means of raised source/drain regions which are formed by epitaxially grown source/drain materials on the semiconductor film of SOI substrates.

In case of the IC layout 100, one dummy gate structure 124 has one active gate structure 122 at each side. In order to avoid interference between neighboring transistor devices, e.g., two adjacent gate structures 122 together with the respective contact regions 107, 108, any dummy gate structure 124 disposed in between is to be shut down.

Figure 2B:
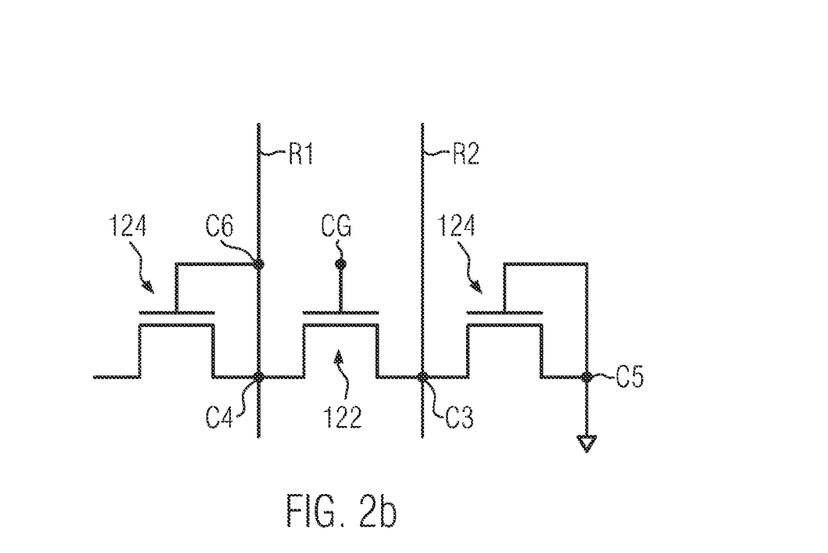

FIG. 2b shows a wiring design for actively shutting down the dummy gate structures 124. As in standard cell designs, the gate structure 122 and the adjacent dummy gate structures 124 are coupled to a rail R1. In case of an NMOS device to be implemented by the gate structure 122 together with respective contact regions, 107, 108, the rail R1 may be the Vss rail. In case of a PMOS device to be implemented, the rail R1 may be the Vdd rail. Furthermore, line R2 in FIG. 2b represents the active node of the transistor device comprising the gate structure 122. In an example, the line R2 may represent the drain contact.

In some examples, where the transistor comprising the gate structure 122 forms an NMOS device, node C5 is coupled to Vss, otherwise, the node C5 is coupled to Vdd. An active shutdown of the dummy gate structures 124 is achieved in connecting one of the dummy gate structures to Vss in case of NMOS devices or Vdd in case of PMOS devices. In this way, an electrical coupling between two neighboring active gate structures 122 in one active region 110 is avoided.

Figure 2C:
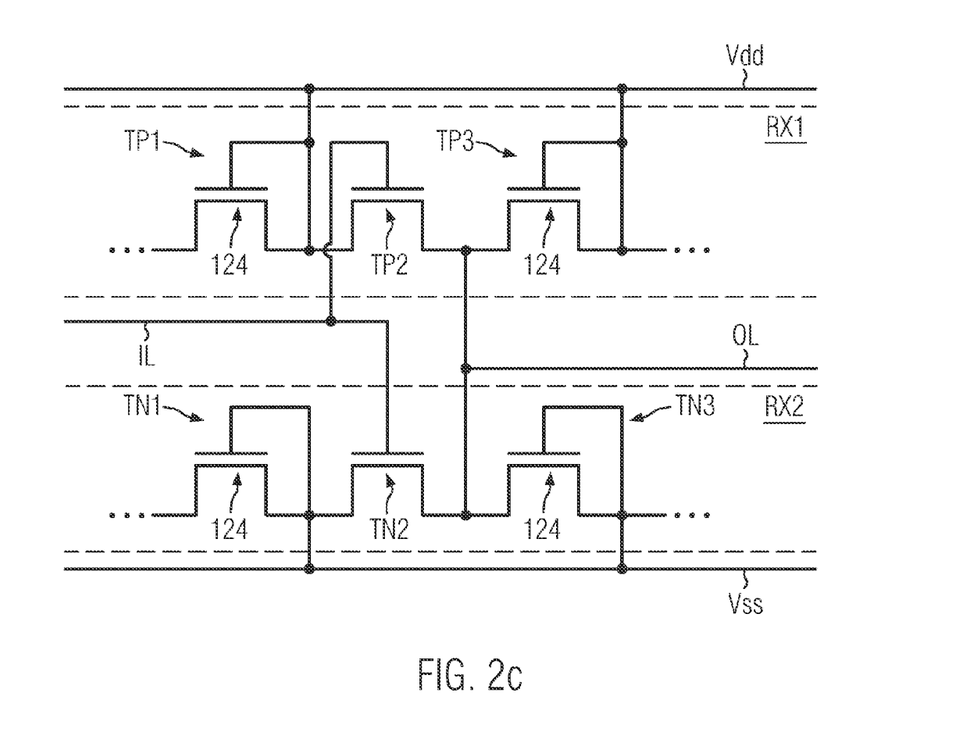
FIG. 2c schematically illustrates an inverter scheme in accordance with some illustrative embodiments of the present disclosure.

FIG. 2c schematically illustrates an inverter scheme in accordance with some illustrative examples of the present disclosure. Transistor devices TP1, TP2, TP3 (optionally more than three), e.g., implemented as PMOS devices, are provided in a first continuous active region RX1, while transistor devices TN1, TN2, TN3 (optionally more than three), e.g., implemented as NMOS devices, are provided in a second continuous active region RX2. An input line IL and an output line OL are coupled to gate and drain of the transistor device TP2, and gate and drain of the transistor device TN2. Couplings to the rails Vss and Vdd are indicated as pointed out above. The transistor devices TN1, TN3, TP1, and TP3 comprise dummy gate structures 124 which are shut down in the inverter schematic as illustrated in FIG. 2c.

In accordance with some illustrative embodiments of the present disclosure, wiring design rule limitations are proposed which allow designing scaled IC layouts without increased area penalties at 28 nm and below, for example. As described below, minimum contact to contact distances and minimum metal line to metal line spacings may be defined.

Referring to FIG. 2a, the active region 110 has a layout, i.e., geometric shape in top view, which is substantially rectangular or strip-like. Furthermore, the active region has one or more extension portions, such as the extension portions 112, 114 and 115. Each of the extension portions 112, 114 and 115 is located at one of the contact regions 108 and protrudes outwardly away from the active region 110. Particularly, the extension portions 112, 114 and 115 basically represent lateral extensions of the contact regions 108 reaching into the surrounding material 105.

As illustrated in FIG. 2a, the extension portions 112, 114 and 115 are formed in a zigzag manner along the length dimension L of the active region 110. That is, the extension portions 112, 115 are provided at one side of the active region 110, while the extension portion 114 is located at an opposing side of the active region 110. In this way, an indention 116 having a depth d1 is provided between the extension regions 112, 115 along the length dimension L at one side of the active region 110. The person skilled in the art will appreciate that several copies of the indention 116 may be provided along each side of the active region 110 in a direction parallel to the L dimension. Accordingly, indentions 116 may be formed at the opposite side of the active region lateral to the extension portion 114, as well, such that indentions 116 and oppositely disposed indentions on the other side are offset relative to each other along the dimension L of the active region 110. In some illustrative examples of the present disclosure, a length l1 of the indention 116 may be substantially equal to a multiple of the CPP parameter, e.g., three times CPP (for a definition of CPP, refer to FIG. 1). Alternatively or additionally, a length l2 of an extension portion, e.g. the extension portion 114, may be substantially equal to CPP. This does not pose any limitation on the present disclosure and an arbitrary multiple of CPP may be chosen for at least one of l1 and l2. The person skilled in the art will appreciate that the depth d1 may be substantially greater than the PC overlap (see FIG. 1) of the gate structures 122 and the dummy gate structures 124. In accordance with some illustrative examples herein, the depth d1 may be greater than the PC overlap, but smaller than 1.5 times the PC overlap. In some illustrative examples, d1 may be greater than the PC overlap and smaller than 2 times the PC overlap or smaller than 5 times the PC overlap or smaller than 10 times the PC overlap. In this way, the design rules imposed by OSEb and/or OSEa may be respected.

In accordance with some alternative embodiments of the present disclosure, the indentions 116 may be only formed at one side of the active region 110, e.g., for only forming at least one of the extension regions 112, 115 or only at least the extension region 114.

As illustrated in FIG. 2a, the extension portions extend into the surrounding non-active region 105 and each of the extension portions 112, 114 and 115 is enclosed at two sides or more by the non-active region 105. In accordance with the depicted illustration, the extension region 112 has edges 117a, 117c that extend into the non-active region 105 relative to the contact region 107. As depicted in FIG. 2a, the edges 117a, 117c may be substantially perpendicular to an edge 118 of the contact region 107, where the extension portion 112 is further delineated by an edge 117b connecting the edges 117a, 117c such that the extension region 112 substantially assumes a box-like shape. This does not pose any limitation on the present disclosure and, alternatively, the edges 117a and 117c may be oriented such that the extension region 112 substantially assumes a triangular shape. The person skilled in the art will understand that, in choosing an appropriate number and orientation of edges, the extension region 112 may be formed with a general polygonal shape (regular or irregular). Accordingly, the extension regions 112, 114, 115 may be formed by at least two edges or at least one kink that peeks into the surrounding non-active region 105. Alternatively, roundings or even sharper tips may be formed instead of the depicted edges/kinks. Furthermore, the edge 117a of the extension region 112 and the edge 118 of the contact region 107 may form a kink that points into the active region 110. Instead of the rather sharp or angled inwardly pointing edges/kinks (e.g., at reference numerals 117a, 118 in FIG. 2a), roundings may be formed in order to avoid tips.

In some illustrative embodiments, the edges 117a, 117c may be settled underneath the dummy gate 124 and/or the gate structure 122, because of a certain overlay tolerance between the active region 110 and the gate structures 122, 124. Accordingly, the extension portions 112, 114, 115 are not allowed to contribute to the active transistor device width, i.e., the width of the active region 110 at the contact area 107, e.g., the drain side of a transistor device formed by the gate structure 122.

In accordance with some illustrative embodiments of the present disclosure, at least one of the gate structures 122 and the dummy gate structure 124 disposed at the extension region 112 partially overlies the extension region 112 so as to overlap the edge(s)/kink(s) 118 of the extension region 112. The person skilled in the art will appreciate that the arrangement of the dummy gate structure 124 and the gate structure 122 at the extension region 112, as illustrated in FIG. 2a, allows for a sufficient landing area for contacts in the contact region 108 and the extension region 112 without giving rise to possible misalignment of contacts in the extension region 112.

With regard to FIG. 2a, contact structures will be described. One or more contact structures C3 are formed in the contact regions 107. In forming a plurality of contact structures C3 within each of the contact regions 107, a more uniform current distribution within the contact region 107 may be reached and the resistance may be reduced, enabling faster transistor devices to be formed in the active region 110.

In accordance with some illustrative embodiments of the present disclosure, at least one contact structure C4 may be provided within each of the contact regions 108, as indicated in FIG. 2a via dashed lines.

A shutting down of the dummy gate structures 124 may be achieved as follows: a contact structure C5 may be formed adjacent to the dummy gate structure 124 at the extension region 112. An according contact structure C6 is formed for contacting the dummy gate structure 124 at the extension region 114. The contact structure C5 (and accordingly the contact structure C6) may be formed so as to simultaneously contact the dummy gate structure 124 and the contact region 108 at the extension region 112. For example, the contact structure C5 may be coupled to a Vss rail (not illustrated) in case an NMOS device is to be realized by the gate structure 122 and the contact regions 108 and 107, thus forming the transistor device T. Alternatively, the contact structure C5 may be coupled to a Vdd rail (not illustrated) when the transistor device T is to be implemented as a PMOS device.

Figure 2D:
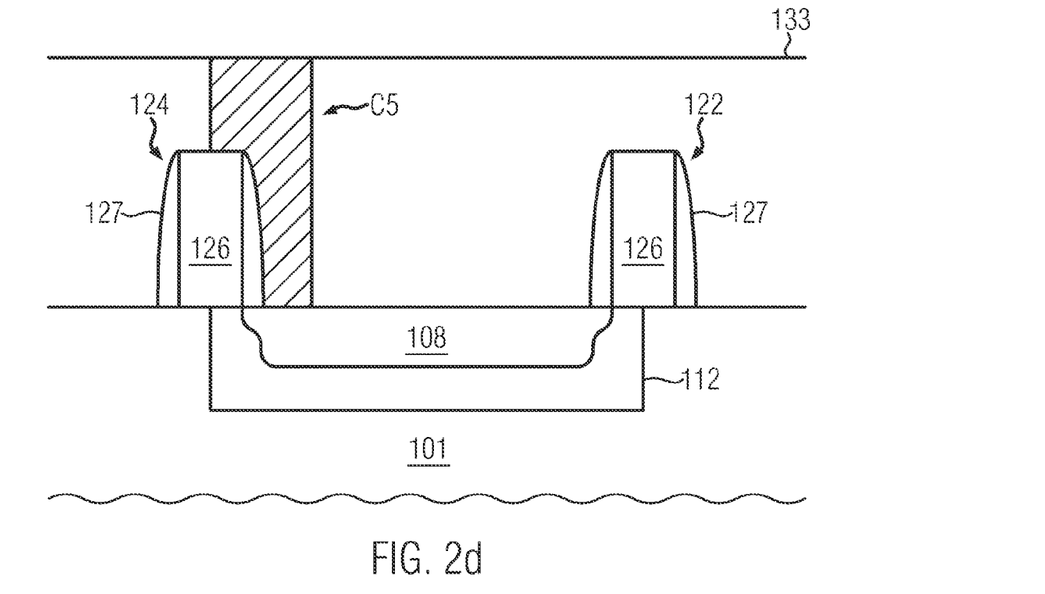

FIG. 2d schematically illustrates a cross-section taken along the line a-a in FIG. 2a. Herein, the gate structure 122 and the dummy gate structure 124 are shown together with the contact structure C5 contacting the dummy gate structure 124 and the extension region 112, i.e., the contact region 108 extending into the extension region 112. Herein, the extension region 112 is provided as a doped region within a semiconductor substrate 101. In FDSOI applications, the extension region 112 may be alternatively formed by an SOI film portion that is laterally enclosed by an insulating structure, while a buried insulating material layer is provided under the SOI film.

As illustrated in FIG. 2d, the gate structure and the dummy gate structure are formed by a gate electrode 126 comprising a gate electrode material, e.g. polysilicon and the like, a high-k gate insulating material, work function adjusting material, and so on.

Furthermore, sidewall spacers 127 may be used for adjusting lateral separations between gate and source/drain regions, source/drain extension regions and the like. The contact C5 may be further embedded into an interlayer dielectric material 133.

Figure 2E:
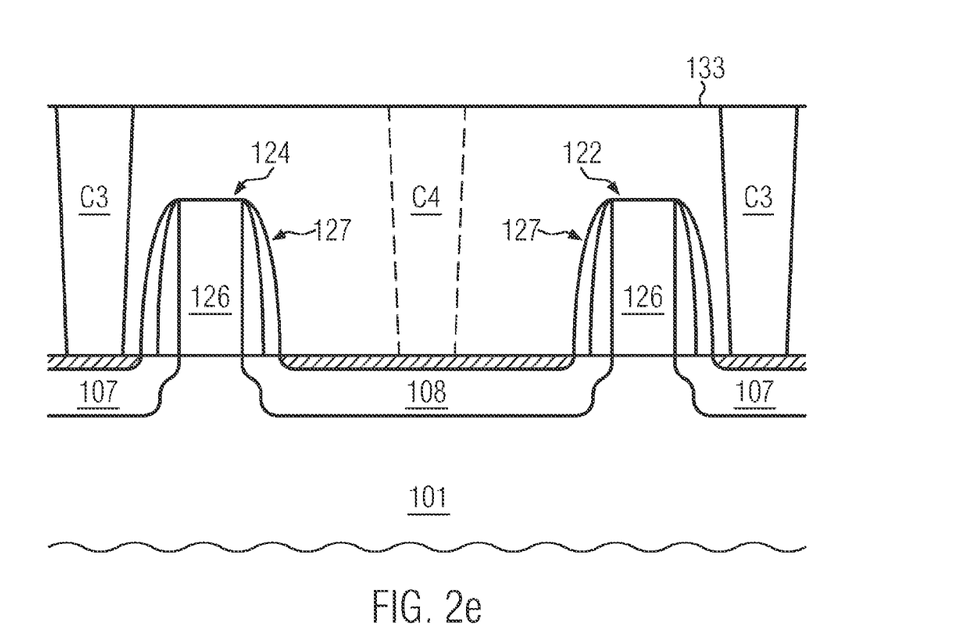

FIG. 2e schematically illustrates a cross-section taken along the line b-b in FIG. 2a. Herein, contacts C3 and optional contacts C4 are schematically illustrated, the contact structures C3, C4 contacting the contact regions 107, 108, e.g., via silicide regions. Alternatively, instead of doped contact regions 107, 108, raised source/drain regions (not illustrated) may be provided.

With regard to FIG. 3, an IC layout 200 in accordance with alternative embodiments of the present disclosure will be described. The IC layout 200 comprises an active region 210 and a plurality of gate structures 222, 224, e.g. gate structures 222 and dummy gate structures 224. Similar to contact structures C3 and C4, contacts C7 and C8 are provided for contacting the active region 210 between the gate structures 222, 224.

Figure 3:
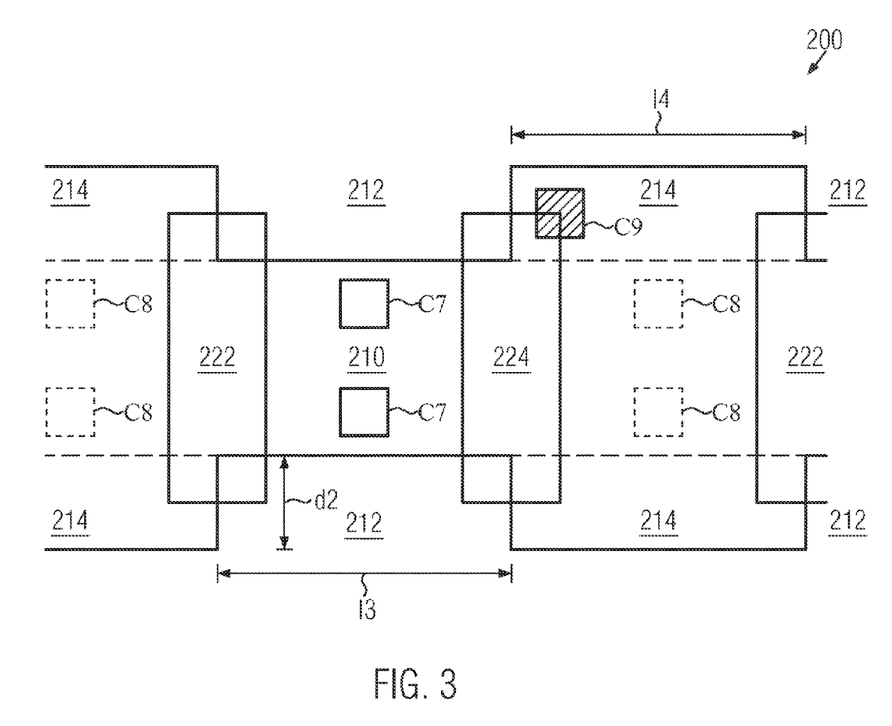
FIG. 3 schematically illustrates an IC layout in accordance with other illustrative embodiments of the present disclosure.

The IC layout 200 as illustrated in FIG. 3 differs from the IC layout 100 as illustrated in FIG. 2a in that extension regions 214 are disposed at opposing sides of the active region 210. Herein the extension regions 214 at opposing sides of the active region 210 are not offset as compared to the extension regions 112, 114, 115 in FIG. 2a. In other words, the active region 210 has indentions 212 that oppose each other when seen along the width dimension W. The extension regions 214 are formed between two indentions 212.

In accordance with the illustration in FIG. 3, a portion of the active region 210 may assume a dog bone shape in top view.

The person skilled in the art will appreciate that the extension regions 214 may be formed in accordance with the extension regions 112, 114 and 115 as described above. In this regard, reference is made to the according description with regard to the configuration of the extension regions 112, 114 and 115. A length 14 of the extension region 214 may be substantially equal to CPP in some explicit examples herein. Additionally or alternatively, a length 13 of an indention 212 may be substantially equal to CPP. A depth d2 of an indention 212 may be substantially chosen in accordance with a depth d1 as described above.

In accordance with the illustration in FIG. 3, a contact structure C9 contacting a dummy gate 224 and the extension region 214 may be realized in analogy to the contacts C5 and C6 as described with regard to FIGS. 2a and 2b above. Similar to the description above, the IC layout 200 may be implemented as a continuous RX configuration as described above. This allows introducing layout limitations in an advantageous manner. The person skilled in the art will appreciate that in choosing a continuous RX configuration, design rules according to OSEa, LOD (SA), LOD (SB), and the like are eliminated and do not need to be considered when going to smaller technology nodes, particularly no effects related to these parameters will become a major influence in continuous RX configurations at lower scales.

The present disclosure provides, in the various aspects as described above, an overlay tolerance for contact placement and reduces the probability of short junctions due to contacts that do not cross the border of the active regions when imposing the extension regions. Furthermore, the present disclosure allows for a standard contact dimensioning and, therefore, does not raise new litho/OPC implications. Furthermore, the various embodiments as described above are applicable to source side dummy transistors, as well as to drain side dummy transistors. The person skilled in the art will appreciate that advantageous implementations of the present disclosure may be achieved in the framework of FDSOI applications at 20 nm and beyond.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A semiconductor device structure, comprising:
   a semiconductor substrate with an active region provided therein;
   a gate structure and a dummy gate structure, both of which are positioned above said semiconductor substrate so as to partially overlie said active region;
   two contact regions provided in said active region for forming source and drain regions, each of which being located at a respective one of two opposing sides of said gate structure, wherein one of said contact regions is further located at one side of said dummy gate structure; and
   a contact structure contacting said one of said contact regions and said dummy gate structure for connecting said one of said contact regions and said dummy gate structure with one of a Vdd rail and a Vss rail;
   wherein, in a top view of said active region, said active region has an extension portion protruding laterally away from said active region relative to said other contact region, said contact structure is located over said extension portion, and said dummy gate structure and said gate structure each partially overlie said extension portion.

2. The semiconductor device structure of claim 1, wherein said extension portion has one or more of a kink, a rounding and a tip reaching into said semiconductor substrate surrounding said active region.

3. The semiconductor device structure of claim 1, wherein a boundary of said extension portion is partially overlain by said dummy gate structure and said gate structure.

4. The semiconductor device structure of claim 1, wherein said contact structure is laterally offset relative to a gate length dimension representing a minimum spacing between source and drain regions, when seen in a top view.

5. The semiconductor device structure of claim 1, wherein said active region has a substantially greater length dimension along a gate length dimension representing a minimum spacing between source and drain regions, when seen in a top view, than a width dimension perpendicular to said gate length dimension.

6. The semiconductor device structure of claim 5, wherein a width dimension of said gate structure and said dummy gate structure is substantially greater than said width dimension of said active region.

7. A semiconductor device structure, comprising:
a semiconductor substrate with an active region provided therein;
a gate structure and a dummy gate structure, both of which are positioned above said semiconductor substrate so as to partially overlie said active region;
two contact regions provided in said active region for forming source and drain regions, each of which being located at a respective one of two opposing sides of said gate structure, wherein one of said contact regions is further located at one side of said dummy gate structure; and
a contact structure contacting said one of said contact regions and said dummy gate structure for connecting said one of said contact regions and said dummy gate with one of a Vdd rail and a Vss rail;
wherein, in a top view of said active region, said active region has a tapered portion and extension portions which laterally protrude away from said active region relative to said tapered portion, said contact structure is positioned above one of said extension portions, and said dummy gate structure and said gate structure each partially overlie said extension portion.

8. The semiconductor device structure of claim 7, wherein said one of said extension portions has one or more of a kink, a rounding and a tip reaching into said semiconductor substrate surrounding said active region.

9. The semiconductor device structure of claim 7, wherein opposing boundary sides of said one of said extension portions extending away from said tapered portion are at least partially overlain by said dummy gate structure and said gate structure.

10. The semiconductor device structure of claim 7, wherein said contact structure is laterally offset into said one of said extension regions relative to a gate length dimension representing a minimum spacing between source and drain regions, when seen in a top view.

11. The semiconductor device structure of claim 7, wherein said active region has a substantially greater length dimension along a gate length dimension representing a minimum spacing between source and drain regions, when seen in a top view, than a width dimension perpendicular to said gate length dimension.

12. The semiconductor device structure of claim 11, wherein a width dimension of said gate structure and said dummy gate structure is substantially greater than said width dimension of said active region.

13. A semiconductor device structure, comprising:
a semiconductor substrate with an active region provided therein;
at least first and second gate structures and first and second dummy gate structures, said first and second gate structures and said first and second dummy gate structures being positioned above said semiconductor substrate so as to partially overlie said active region, wherein said first and second gate structures and said first and second dummy gate structures are provided in a successive manner;
at least five contact regions provided in said active region such that each of said first and second gate structures and each of said first and second dummy gate structures has respective source and drain regions formed by said contact regions at opposing sides thereof, wherein a first one of said contact regions is further located at one side of said first dummy gate structure and a second one of said contact regions is further located at one side of said second dummy gate structure; and
at least two contact structures, each of which contacting one of said contact regions being enclosed by one of said first and second gate structures and one of said first and second dummy gate structures for connecting said first one of said contact regions together with said first dummy gate structure and said second one of said contact regions together with said second dummy gate structure, wherein each of said at least two contact structures is connected to one of a Vdd rail and a Vss rail;
wherein, in a top view of said active region, said active region has at least two extension portions protruding laterally away from said active region relative to said other contact region, said contact structure being located over said extension portion and said first and second dummy gate structures and said first and second gate structures each partially overlie one said extension portions; and
wherein, between two successive contact portions with a respective one of said extensions portions, there is at least one contact portion without an extension portion.

14. The semiconductor device structure of claim 13, wherein each of said extension portions has one or more of a kink, a rounding and a tip reaching into said semiconductor substrate surrounding said active region.

15. The semiconductor device structure of claim 13, wherein a boundary of said respective one of said extension portions is partially overlain by a respective one of said first and second dummy gate structures and said first and second gate structures.

16. The semiconductor device structure of claim 13, wherein each of said contact structures is laterally offset relative to a gate length dimension representing a minimum spacing between source and drain regions, when seen in a top view.

17. The semiconductor device structure of claim 13, wherein said semiconductor device structure is formed in accordance with FDSOI techniques at 28 nm or beyond.

* * * * *